US012611110B2

(12) United States Patent
Pflug et al.

(10) Patent No.: US 12,611,110 B2
(45) Date of Patent: Apr. 28, 2026

(54) APPARATUSES AND METHODS FOR PROVIDING A SCORE INDICATIVE OF A PHYSIOLOGICAL CONDITION OF AT LEAST ONE INDIVIDUAL

(71) Applicant: Sony Group Corporation, Tokyo (JP)

(72) Inventors: Anja Pflug, Tokyo (JP); Thomas Carette, Tokyo (JP)

(73) Assignee: Sony Group Corporation, Tokyo (JP)

( * ) Notice: Subject to any disclaimer, the term of this patent is extended or adjusted under 35 U.S.C. 154(b) by 480 days.

(21) Appl. No.: 17/583,219

(22) Filed: Jan. 25, 2022

(65) Prior Publication Data

US 2022/0240798 A1       Aug. 4, 2022

(30) Foreign Application Priority Data

Feb. 2, 2021     (EP) ..................................... 21154833

(51) Int. Cl.
*A61B 5/00*          (2006.01)
*A61B 5/0205*      (2006.01)
                        (Continued)

(52) U.S. Cl.
CPC ........ *A61B 5/02055* (2013.01); *A61B 5/0215* (2013.01); *A61B 5/02405* (2013.01); *A61B 5/02438* (2013.01); *A61B 5/0816* (2013.01); *A61B 5/11* (2013.01); *A61B 5/165* (2013.01); *A61B 5/4803* (2013.01); *A61B 5/4809* (2013.01); *A61B 5/4818* (2013.01); *A61B 5/7267* (2013.01); *A61B 5/7275* (2013.01); *G16H 50/20* (2018.01)

(58) Field of Classification Search
CPC .............. A61B 5/02055; A61B 5/0215; A61B 5/02405; A61B 5/02438; A61B 5/0816; A61B 5/11; A61B 5/4803; A61B 5/4809; A61B 5/4818; A61B 5/7267; A61B 5/7275; A61B 2503/20
See application file for complete search history.

(56) References Cited

U.S. PATENT DOCUMENTS

2009/0157660 A1      6/2009  Jung et al.
2013/0012802 A1      1/2013  Horseman
                     (Continued)

OTHER PUBLICATIONS

Lockchain and Health IT: Algorithms, Privacy, and Data; Office of the National Coordinator for Health Information Technology U.S. Department of Health and Human Services; Allison Ackerman Shrier, Anne Chang, Nadia Diakun-thibault, Luca Forni, Fernando Landa, Jerry Mayo, Raul van Riezen Project Pharm (Year: 2016).*
(Continued)

*Primary Examiner* — Sana Sahand
(74) *Attorney, Agent, or Firm* — XSENSUS LLP

(57)          ABSTRACT

The present disclosure relates to a concept for providing a score indicative of a physiological condition of at least one individual. The concept include measuring physiological or behavioral data of the individual, determining contextual data comprising a measurement context and/or socio-demographic features associated with the individual determining a metric based on the measured physiological or behavioral data, and determining the score by comparing the metric against a predicted value from a prediction model trained with the contextual data.

15 Claims, 2 Drawing Sheets

(51) Int. Cl.

| | | |
|---|---|---|
| *A61B 5/0215* | (2006.01) | |
| *A61B 5/024* | (2006.01) | |
| *A61B 5/08* | (2006.01) | |
| *A61B 5/11* | (2006.01) | |
| *A61B 5/16* | (2006.01) | |
| *G16H 50/20* | (2018.01) | |

(56) References Cited

U.S. PATENT DOCUMENTS

| | | | |
|---|---|---|---|
| 2017/0206795 A1* | 7/2017 | Kaleal, III | G16H 40/63 |
| 2018/0303396 A1* | 10/2018 | Wild | G16H 10/60 |
| 2020/0375533 A1* | 12/2020 | Bissen | G16H 50/50 |
| 2021/0104332 A1* | 4/2021 | Kåberg Johard | G16H 50/50 |

OTHER PUBLICATIONS

Vincent, "Samsung's 'Artificial Humans' are Just Digital Avatars", Available Online at:https://www.theverge.com/2020/1/7/21051390/ samsung-artificial-human-neon-digital-avatar-project-star-labs, Jan. 7, 2020, 4 pages.

* cited by examiner

Fig. 1

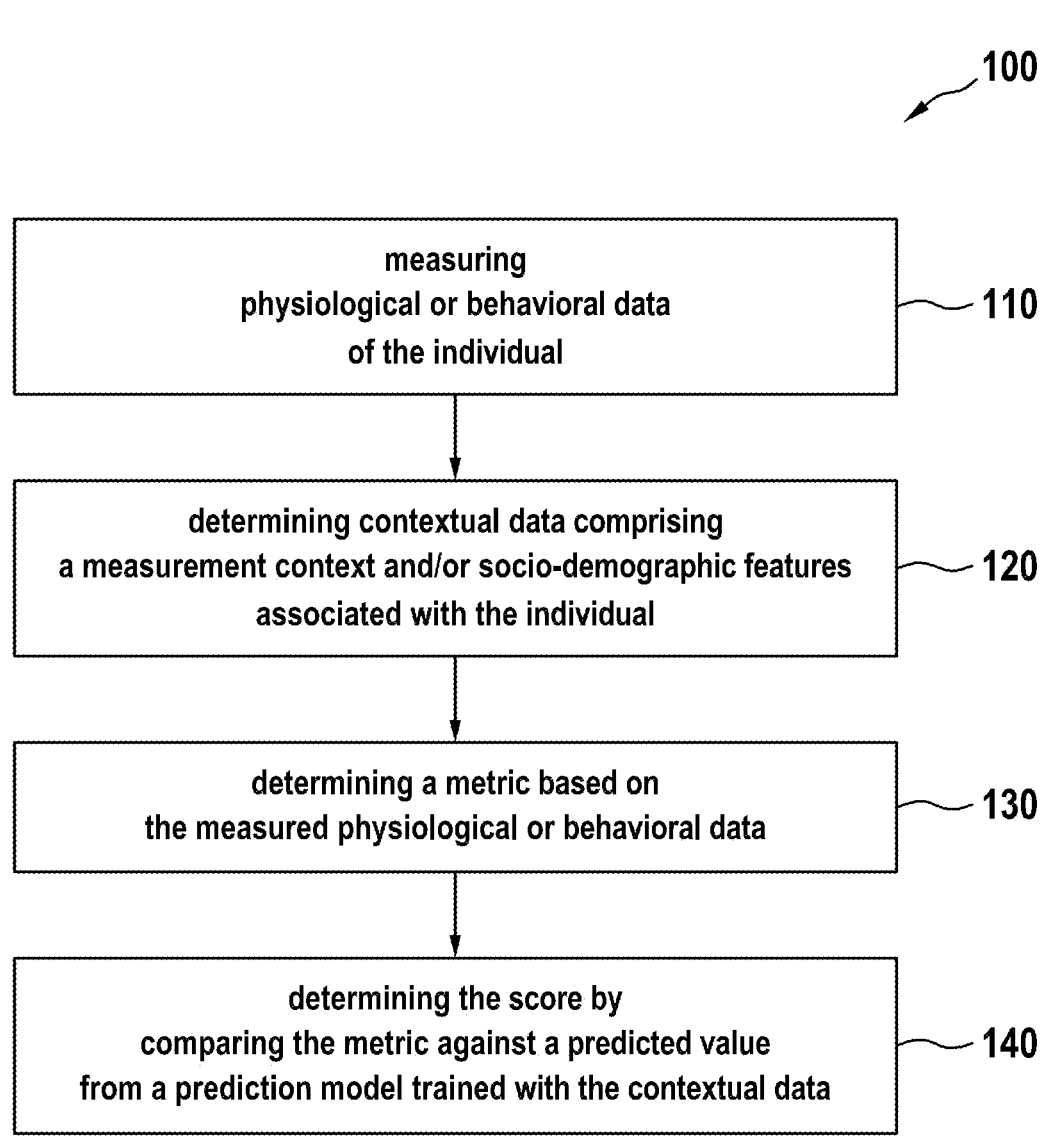

100 measuring
physiological or behavioral data
of the individual — 110 determining contextual data comprising
a measurement context and/or socio-demographic features
associated with the individual — 120 determining a metric based on
the measured physiological or behavioral data — 130 determining the score by
comparing the metric against a predicted value
from a prediction model trained with the contextual data — 140

APPARATUSES AND METHODS FOR PROVIDING A SCORE INDICATIVE OF A PHYSIOLOGICAL CONDITION OF AT LEAST ONE INDIVIDUAL

CROSS-REFERENCE TO RELATED APPLICATION

This application claims priority from EP 21154833.4, filed on Feb. 2, 2021, the entire contents of which are incorporated herein by reference.

FIELD

The present disclosure generally relates to apparatuses and methods for measuring a physiological condition of individuals and, more particularly, for providing a score indicative of a physiological condition of one or more individuals.

BACKGROUND

For one example, Covid-19 pandemic has changed the way people are working. An increasing number of employees stay at home, making remote or home office the norm. However, this change might also affect the way employees are able to distinguish between work and free time and impact their stress coping abilities. To be able to compare strategies of companies using time-management tools, a systematic approach may help to distinguish unrelated changes from affective changes, for example.

Also, in the last years, consumers are more and more interested in buying ethical and economic products. This includes taking care of workers conditions. Certificates may help them to decide which products they are going to trust, however, there is no direct link from workers wellbeing to any certificate. Using worker questionnaires for building such a certificate would be problematic since there is no guarantee that they are not manipulated. Consumers and potential new employees would need an objective method to judge companies' responsibilities for their workers.

For another example, the worldwide happiness index tries to estimate quality of life for different countries. It calculates for 156 countries how happy their citizens perceive themselves to be. Founded in 2011 the top five countries are European. The index is based on questionnaires and a few sociodemographic statistics. However, how lucky you are rating yourself depends also on how you think how lucky you are compared to other countries (I should be lucky because I have enough to eat, while they don't). This induces a perceptual bias into the index and might overwrite other factors to be happy like meeting friends, enjoy conversations, sleep well, have an active life, or feel self-confident inside your community. For example, the happiness index is not directly anti-correlated to the amounts of suicides.

Thus, there is a demand for a systematic and objective approach for indicating the quality of life of individuals, such as employees, for example. In this regard, a further demand is privacy preservation.

SUMMARY

This demand is addressed by apparatuses and methods in accordance with the independent claims. Possibly advantageous embodiments are addressed by the dependent claims.

According to a first aspect, the present disclosure proposes a method for providing a score indicative of a physiological condition of at least one individual. The method includes measuring at least one physiological or behavioral parameter (physiological or behavioral data) of the individual. Further, contextual information is determined, the contextual information comprising a measurement context and/or socio-demographic features associated with the individual. The method further includes determining a metric based on the at least one measured physiological or behavioral parameter. The metric is then compared against a predicted value from a prediction model trained with the contextual information to determine the score.

In some embodiments, the at least one physiological or behavioral parameter is measured with one or more sensors of an electronic device associated with the individual, such as a personal electronic device. Thus, the measurement may be done in a comfortable way at a personal level.

In some embodiments, the electronic device comprises at least one of a smartphone, a camera, a microphone, a wearable device configured to detect body signals of the individual, or an electronic device implanted in the body of the individual. Thus, the electronic device may be a device the individual already uses in other situations of daily life.

In some embodiments, measuring the at least one physiological or behavioral parameter includes measuring the parameter in a hospital, at home, at a workplace, or during commuting of the individual. In some embodiments, measuring the at least one physiological or behavioral parameter includes measuring the parameter during working hours and/or during resting hours of the individual. Thus, the at least one physiological or behavioral parameter may be measured in authentic situations of the daily life of the individual.

In some embodiments, measuring the at least one physiological or behavioral parameter includes measuring at least one of a heart rate, heart rate variability, sleep apnea events, sleep metrics, blood pressure, body temperature, movement pattern, speech, respiration rate, brain signals, skin conductance, eye movements, arousal levels, social contacts. Any of those parameters may be indicative of the quality of life of individuals.

In some embodiments, adding contextual information includes associating a personal identifier of the individual with the individual dataset. A personal identifier may allow associating more contextual information related to the individual to the measured parameter(s). For example, adding contextual information may include adding, based on the personal identifier, socio-economic or socio-demographic features of the individual to the individual dataset.

In some embodiments, the socio-demographic features of the individual are extracted from at least one of an employer's human resources database or a doctor's patient database.

In some embodiments, the socio-demographic features comprise at least one of an age, gender, number of children, job position, salary, a body mass index, current medication, anamnesis, size of country, size of city, income, education level of the of the individual. All this may influence the measured physiological or behavioral parameter(s) or put them in an actual living context of the individual.

In some embodiments, the method further includes applying one or more privacy preservation algorithms to the contextual information. In this way, the individual's data and privacy may be protected. For example, the privacy preservation algorithms may comprise at least one of a blockchain algorithm, a local differential privacy algorithm or a multiparty computation algorithm.

In some embodiments, the method further includes training model parameters of the prediction model based on contextual information of a plurality of individuals. In some embodiments, the prediction model may be implemented using machine learning technology predicting one or more physiological or behavioral parameters or a metric derived thereof based on provided contextual information of an individual. Thus, embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. By training a machine-learning model using training contextual information and a desired output (e.g., a welfare metric), the machine-learning model "learns" a transformation between the contextual information and the metric, which can be used to provide an output based on actual nontraining contextual information provided to the machine-learning model. The provided data (e.g. physiological or behavioral parameters and contextual information) may be preprocessed to obtain a feature vector, which is used as input to the machine-learning model.

In some embodiments, training the model parameters is performed at a central entity (for example, a cloud server). After training, the trained model parameters and/or a predicted physiological or behavioral parameter may be provided from the central entity to a personal device of the individual for comparing the metric against the predicted value. Thus, the metric may be compared against the predicted value locally at the individual's personal device.

In some embodiments, comparing the metric against the predicted value includes feeding the contextual information in a trained prediction model to generate a predicted physiological or behavioral value based on the contextual information. This may be done locally at the individual's personal device or at a central entity (for example, a cloud server).

In some embodiments, comparing the metric against the predicted value comprises computing a difference or ratio between the metric and the predicted value. In this way, a deviation of the individual's metric from a norm or an expected value can be determined. This in turn may lead to a score indicative of the individual's quality of life.

In some embodiments, the method further includes aggregating scores of different associated individuals to a group score. For example, individual scores of employees of a company or certain departments thereof may be aggregated to a company score indicative of the quality of life or welfare of the company's employees.

In some embodiments, aggregating the individual scores comprises applying one or more privacy preservation algorithms to the individual scores. In this way, the individual's data and privacy may be protected. For example, the privacy preservation algorithms may comprise at least one of a blockchain algorithm, a local differential privacy algorithm or a multi-party computation algorithm.

In some embodiments, the method further includes certifying a group of associated individuals (for example, a company) if its associated group score meets a predefined target. In this way, for example, a company may objectively measure its employees work-life-balance or health condition and get certified if the employees are in good condition.

According to a further aspect, the present disclosure proposes a system for providing a score indicative of a physiological condition of at least one individual, wherein the system is configured to measure at least one physiological or behavioral parameter of the individual, determine contextual information comprising a measurement context and/or socio-demographic features associated with the individual, determine a metric based on the at least one measured physiological or behavioral parameter, and determine the score based on a comparison of the metric against a predicted value from a prediction model trained with the contextual information.

Embodiments of the present disclosure may enable creating an objective certificate which indicates the quality of life (for example, of workers) based on a combination of unbiased, personalized models with privacy preservation.

BRIEF DESCRIPTION OF THE FIGURES

Some examples of apparatuses and/or methods will be described in the following by way of example only, and with reference to the accompanying figures, in which FIG. 1 shows a flowchart of a method for providing a score indicative of a physiological condition of at least one individual in accordance with embodiments of the present disclosure.

DETAILED DESCRIPTION

Figure 2:
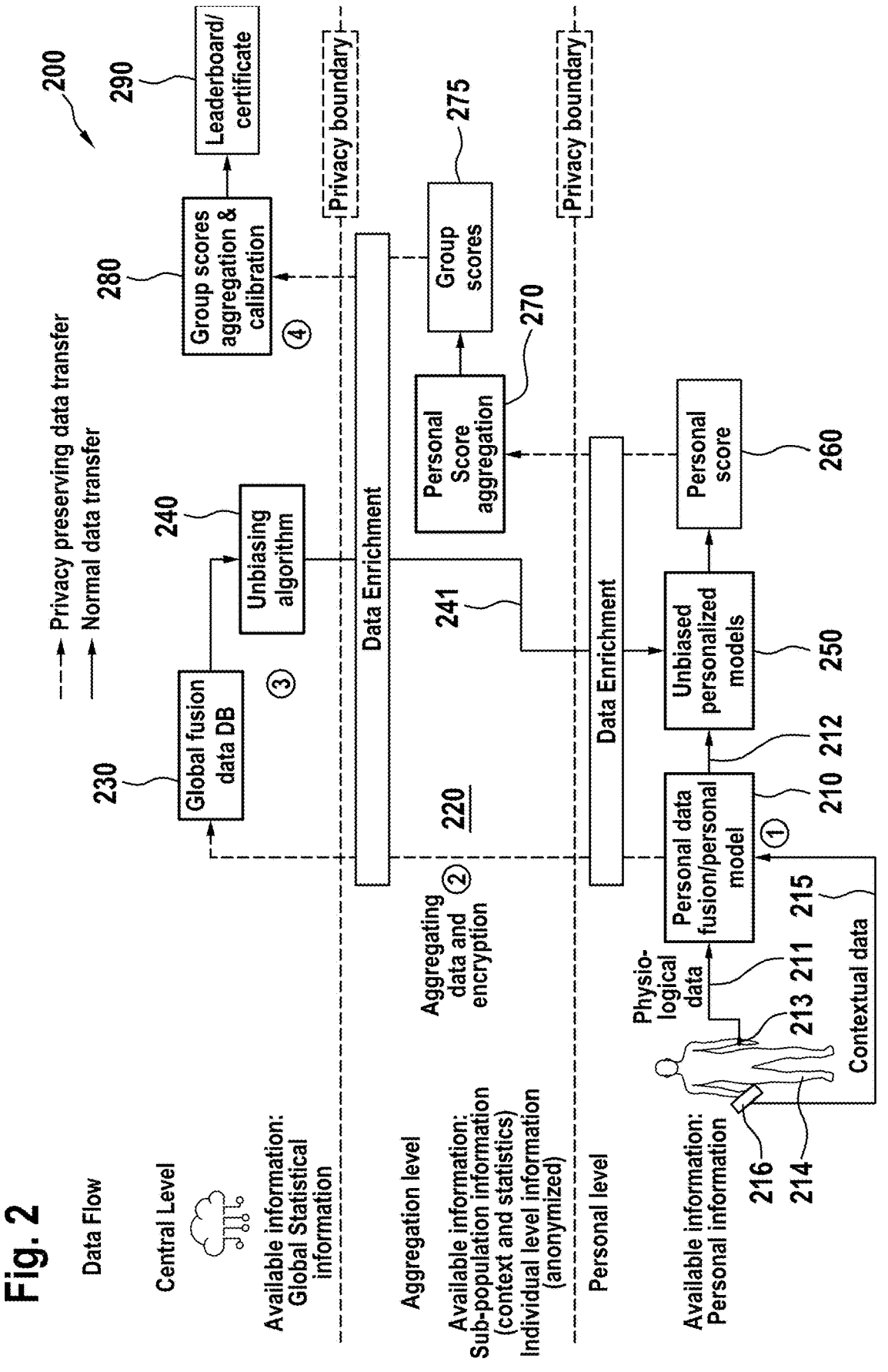
FIG. 2 shows a system implementing an embodiment of the method of FIG. 1.

Some examples are now described in more detail with reference to the enclosed figures. However, other possible examples are not limited to the features of these embodiments described in detail. Other examples may include modifications of the features as well as equivalents and alternatives to the features. Furthermore, the terminology used herein to describe certain examples should not be restrictive of further possible examples.

Throughout the description of the figures same or similar reference numerals refer to same or similar elements and/or features, which may be identical or implemented in a modified form while providing the same or a similar function. The thickness of lines, layers and/or areas in the figures may also be exaggerated for clarification.

When two elements A and B are combined using an 'or', this is to be understood as disclosing all possible combinations, i.e. only A, only B as well as A and B, unless expressly defined otherwise in the individual case. As an alternative wording for the same combinations, "at least one of A and B" or "A and/or B" may be used. This applies equivalently to combinations of more than two elements.

If a singular form, such as "a", "an" and "the" is used and the use of only a single element is not defined as mandatory either explicitly or implicitly, further examples may also use several elements to implement the same function. If a function is described below as implemented using multiple elements, further examples may implement the same function using a single element or a single processing entity. It is further understood that the terms "include", "including", "comprise" and/or "comprising", when used, describe the presence of the specified features, integers, steps, operations, processes, elements, components and/or a group thereof, but do not exclude the presence or addition of one or more other features, integers, steps, operations, processes, elements, components and/or a group thereof.

FIG. 1 schematically illustrates a flowchart of a method 100 for providing a score indicative of a physiological condition of at least one individual.

Method 100 includes measuring 110 at least one physiological or behavioral parameter of the individual. Examples of physiological parameters are heart rate, blood pressure, body temperature, serum levels of various hormones of biomarkers (e.g., stress) and immunological functions. Behavioral parameters can be of mental (e.g., mental conditions), physical, or social nature. Specific examples of behavioral parameters are sleep apnea events, time to fall asleep, movement pattern, speech, respiration rate, or social contacts of a human. The skilled person having benefit from the present disclosure will appreciate that these examples are not exhaustive. Physiological and/or behavioral parameters can be used to assess welfare of the individual. However, physiological and/or behavioral parameters, such as heart rate, also depend on the context the individual is facing during measurement. For example, a heart-rate-variability (HRV) depends also on age—younger people tend to have a higher HRV compared to older people. High blood pressure may be caused be certain medication. Therefore, it may not be feasible to consider a physiological or behavioral parameter to assess welfare without placing it into an adequate context.

For this purpose, method 100 further includes determining 120 contextual information comprising a measurement context and/or socio-demographic features associated with the individual. For example, the measurement context may relate to a time of the measurement (for example, day/night), a location of the measurement (for example, high or low elevation), socio-demographic features may relate to an age, gender, number of children, job position, salary, a body mass index, current medication, anamnesis, size of country, size of city, income, or an education level of the individual.

Method 100 further includes determining 130 at least one metric based on the at least one measured physiological or behavioral parameter. For example, a welfare metric may be determined based on a combination of a plurality of different measured physiological and/or behavioral parameters according to a predefined mathematical function. For example, when people are stressed, multiple physiological and behavioral parameters change, many of which can be measured during sleeping. Those are lower heart-rate-variability (HRV), problems falling asleep or sleep apnea (stop breathing during sleep). In one example, those three parameters may be combined in a stress metric. For example:

$$\text{stress} = (\text{amount of decrease in HRV} * nr \text{ of detected sleep apnea events})/\text{minutes it takes to fall asleep}$$

Method 100 further includes determining 140 a (welfare) score based on a comparison of the determined metric with a predicted value from a prediction model trained with the contextual information associated with the individual or a plurality of individuals. This comparison may also be referred to a unbiasing the determined (biased) metric. For example, the contextual information of the individual may be fed in a trained prediction model to generate a predicted metric based on the contextual information. Comparing the determined (biased) metric with the predicted metric may comprise computing a difference or ratio between the metric and the predicted metric, for example. The ratio or the difference may then lead to the score.

While the acts 110 to 140 of method 100 may be carried out with one or more electronic (personal) devices of the individual, some embodiments may still require some interaction with one or more remote entities, such as databases and/or central servers, for example. This will be explained in more detail in the following.

FIG. 2 shows a system 200 for generating a company welfare certificate using the concept proposed herein. System 200 comprises multiple levels: a personal level, an aggregation level, and a central level.

In the illustrated example, it may be assumed that a provider of HR (human resources) analytics services offers an application (App) to be integrated in employee's electronic devices to collect information, compute metrics and scores (for example, stress scores). The provider may be responsible for centralization of data and its processing (for example, in the cloud). Furthermore, the provider may have several companies as customers each of which has some control over the data uploaded by its employees to a central server. In the illustrated example, this control is used to enrich the employee data with extra HR information, and for final anonymization of the data before transferring it to the provider.

Reference numeral 210 denotes a collection of physiological data 211 and contextual data 215 from wearables (wristband, chest-belt, ring, smartphone, . . . ) and/or stationary sensors (computer camera, microphones, smart matrass, key logger, . . . ) like heart dynamics (PPG, LDF, ECG), skin responses, temperature, movement patterns, mimics, gestures, respiration, voice signal and others during life. At 210, physiological or behavioral data 211 may be collected at the personal level, and a (biased) metric (e.g. stress metric) may be extracted based on the collected physiological or behavioral data 211. For example, the physiological or behavioral data 211 may be measured with one or more sensors of an electronic device 213 associated with the individual 214. Here, the electronic device 213 measuring the physiological or behavioral data 211 is a wearable device (for example, a smart wristband) configured to detect body signals of the individual 214. Alternatively, or additionally, the electronic device 213 may also comprise a smartphone, a camera, a microphone, or an electronic device implanted in the body of the individual, just to name a few examples. From the raw physiological or behavioral data 211 features may be extracted and normalized by the individual's 214 historical data (personal model). The normalized features may be used for creation of different metrices (sleep quality, stress level, health level, fitness level, quantity of social contacts, . . . ). Examples of raw physiological or behavioral data 211 are raw sensor data like ECG, EEG, PPG, GSR, audio, etc. Examples of extracted features are heart rate, mean phasic values, pitch, volume, etc. A metric may be a logic combination of features or may be built with machine learning models, for example, sleep quality, work-life balance, etc.

Additionally, contextual data 215 indicative of a measurement context and/or socio-demographic features associated with the individual 214 may be provided at the personal level. The contextual data 215 may be provided via the same electronic device 213 or another personal electronic device 216 associated with the individual 214. For example, electronic device 216 may be a smartphone which may provide a time and/or location of the physiological or behavioral measurement as well as further personal socio-demographic features of the individual 214 stored in the electronic device 216, such as age, gender, body mass index, online social networking information or the like.

In the data collection and metrics extraction 210, information from physiological measures 211 may be combined with contextual data 215. For example, the time of day and user is lying in bed can be used as context information. Given that it is night, and the individual 214 is not active, physiological or behavioral parameters may be computed. For measuring HRV, for one example, individual heart beats may be detected and the standard deviation of the interbeatintervals within a given time window of multiple minutes may be calculated. One solution could be based on data collected with a wristband in which optical changes due to blood-flow are used to detect the single beats (e.g. PPG), a method which is already in use in multiple wristbands. Sleep apnea events can be detected by extracting respiration patterns from the blood-flow changes and train a classifier to detect moments without breathing (multiple papers on this topic). An alternative could also be to detect snoring breaks using an audio signal. Sleep stages can be predicted based on patterns from accelerometer and heart rate both available by using a wristband 213. Minutes it takes to fall asleep may be computed from the time the individual 214 lays down with eyes closed until first deep sleep phase is detected. In addition, contextual information 215 can be extracted from other sensor data. Activity detection (running, resting, etc.), which strongly affect blood flow, can be deduced from accelerometer data. Also, it is possible to detect if a user is home or at the office using GPS data.

The collected physiological or behavioral data 211 and the associated contextual data 215 may form a personal dataset 212 which may be at least in part forwarded to signal processing block 250 for further processing at the personal level. Signal processing block 250 is configured to compare the individual's actual metric against a predicted value from a prediction model trained with the contextual information. In the following, it will be explained how the predicted value and/or the prediction model may be determined.

For this purpose, additional processing of the collected physiological or behavioral data 211 and/or the associated contextual data 215 may be done at an aggregation and anonymization level 220 before disclosing this information to other parties. Aggregation and anonymization level 220 may aggregate measurement data coming from a plurality of individuals to generate statistical data. For example, the aggregation and anonymization level 220 of system 200 may involve an employer or a doctor of the individual 214. To allow the employer to enrich the data coming from the personal level with extra HR information, the data (physiological/behavioral and/or contextual data) sent by the personal device 213, 216 may be accompanied with a personal identifier such as an employee ID. Thus, the contextual information 215 may comprise a personal identifier of the individual 214. Furthermore, because the collected physiological/behavioral and contextual data is private and thus potentially sensitive, it may be desirable that the aggregation level 220 does not have direct access to it. Depending on the embodiment, the privacy of the individual 214 may be protected either in the communicated data (e.g. Local Differential Privacy, Multi-Party Computation), or by using a secured infrastructure (e.g. blockchain, personal datastore). In some embodiments, Local Differential Privacy (LDP) may be used. LDP adds controlled noise to the collected physiological/behavioral and contextual data (e.g. generalized randomized response on categories and Laplacian noise on continuous variables). This allows to reduce the information carried by individual records while still enabling statistical analysis on large datasets at a central level. At the aggregation and anonymization level 220 more socio-demographic data may be added to the data coming from the personal level, such as age, gender, number of children, job position, salary of the individual, a body mass index, current medication, anamnesis, size of country, size of city, income, education level, etc. In some embodiments, no encryption is used on the data. Rather, the personal identifier may be dropped from the data and it may be relied on the LDP noise to guarantee the anonymity of the individuals. Data may be collected over longer time periods (multiple months to years) to also be able to estimate changes over time and thereby understand effects of strategic decisions (e.g. layoff periods).

At 240, the measured individual (biased) user metrics may be transformed into an unbiased value 241 using aggregated global reference statistics as training data coming from a plurality of individuals and stored in a central database 230. For example, an unbiased value (metric) 241 may be obtained by feeding the aggregated contextual information coming from aggregation and anonymization level 220 in a trained prediction model, for example a machine-learning model, to generate a predicted, unbiased metric 241 based on the aggregated contextual information. Thus, the unbiased metric 241 may be regarded as an expected value given the aggregated contextual information from the individual 214. The unbiasing algorithm may be necessary to compare individuals of different age or gender. This may also allow the individual 214 not to share all of his data to a central level (e.g. cloud) for creating the unbiased values, but to share just enough to create an unbiased model that may be applied, in signal processing block 250, on private data 212 that is never shared. Thus, training the model parameters may be performed at a central entity and, after training, the trained model parameters and/or a predicted metric 241 may be provided from the central entity to a personal device 213, 216 of the individual 214 for comparing the individual's (actual) metric against the predicted value.

For training the model parameters, the (distorted) features and the (distorted) measured signals may be used as covariates to a desired score. Then the variances associated to one or more of the features may be removed from the estimated corrected score (on the user device, signal processing block 250). The distortion may be the result of any measure taken to preserve privacy. For example, a resting heart rate may be predicted based on age and gender with a regression algorithm.

At the central level, the full dataset including the physiological/behavioral data and the contextual data may be used to train regression models for every metric individually. Taking, for example, the HRV as the predicted value, the input features may be contextual information such as age and gender. Trained models may then be sent back to the personal level where a residual between the actual HRV and the predicted HRV is determined by comparison. As a result, an unbiased personal (stress) score 260 may be created. It is independent from age or gender, thus unbiased.

At 270, personal scores 260 of different individuals may be aggregated to a group score 275 at aggregation level. For example, a stress score and data from all employees of one company may be combined into a group score, again respecting the privacy of each individual 214 to prevent identification of single members in small groups (somebody joining a small company). At 280, group scores 275 of different groups may be aggregated to a further higherlevel score 285. At 290, a company or group of people may get certified if its associated score 285 meets a predefined target.

Embodiments of the present disclosure could, for example, be used to evaluate a working environment (office) by determining a score for indicating how healthy (mental and physical) the working environment is. Input data could be physiological or behavioral data from wearables, screen cameras, key loggers, audio signals, agendas. Example metrics are Disturbances Noise, air pollution, stressful schedules, interruptions during concentration time Workflow Concentration possible, stress metrics low, attention from camera Respectfulness Can speak during meetings, . . . .

Communication

Balance between quiet work and collaboration

Static balance

Measures the amount of sitting and standing time, positions which are un-optimal Individual scores 260 indicating the individual quality of the working environment may be aggregated and used to build a company score 275 or 280 indicating the quality of the working environment depending on different scenarios (e.g. high stress levels during meetings (85%), good communication within teams (90%), . . . ). These numbers can then be reported by the company either to take part in a competition (best employer, certificate for taking care of employees) and can also be used internally in the HR department to follow up strategical changes.

Embodiments of the present disclosure could, for example, also be used to understand how happiness is coupled to measurable data, then transfer it to a score. Input data could be physiological or behavioral data from GPS and context data from phones, environmental sensors (air pollution, noise, . . . ), wearable data, etc. To understand what makes people happy, conelations between metrics and reported happiness score could be checked. Example metrics are:

Quality of environment

Noise, air pollution, weather, UV-light, . . . .

Health parameter

Quality of sleep

Level of stress

Vital sign parameters (HR, temperature, respiration rate, . . . )

Static balance

Physical activity vs sitting

Communication

How many people do you communicate with?

Statistics calls/messages

To be able to create an objective happiness index, embodiments propose to measure changes of physical, audio and video signals to estimate the amount of happiness per person. This may lead to an index which represents not "I am happy because I am in a good condition" but, "I am happy because I feel happy" (show the unbiased signs of happiness). To create the index different metrics may be combined (amount of smiling, joyful sounds, joyful movements, sleep quality, . . . ). Like in the use-case before also here data may be unbiased using data within comparable groups (age, gender, . . . ) and data privacy is preserved. In the beginning there could be one step to train the metrics based on questionnaires. Individual happiness scores may be aggregated and used to build a happiness index. These numbers may be reported in the world happiness report and can also be used to understand what humans need to be happy.

Note that embodiments of the present disclosure could, for example, also be used to understand if medical interventions change a quality of life index.

A key feature of embodiments of the present disclosure is the enabling of a calibrated score across diverse subject population. This is done by transforming an initial metric into an unbiased version which is used to produce the user score 260. This allows the user not to share all of his data to the cloud for creating the unbiased scores, but to share just enough to create an unbiased model that is applied on private data that is never shared.

The upstream aggregation steps see private information uploaded to the aggregation level then the central level. Those instances may be characterized by different security and corresponding privacy requirements. The aggregation level may have access to individual records while the central level should only access sub-population statistics. This can be handled using currently existing privacy preserving technologies (local differential privacy, multi-party computation, federated learning, etc.). In some embodiments, it is proposed to collect information at the aggregation level using all the privacy budget available while optimizing data transfer from aggregation level to the central level to minimize the privacy leakage to the central instance.

The central level may store the aggregated data which besides the metric (e.g. sleep time) includes socio-demographic features. For the unbiasing step there are two approaches possible which are both tractable with sensitive data:

1) Data may be clustered (e.g. K-means) in an unsupervised fashion to group subjects. Actual datapoints may be compared within group distribution. Unbiased score 241 may then be represented as percentile value and send back to the personal level 2) Statistics from the aggregation levels are used to train population-based regression models. Models may then be sent back to the aggregation level where the unbiasing may take place. The actual datapoint may be used for score prediction. A residual between prediction and actual value will be used as unbiased score Note that the present technology can also be configured as described below.

Example 1 is a method for providing a score indicative of a physiological condition of at least one individual, the method comprising measuring physiological or behavioral data of the individual, determining contextual data comprising a measurement context and/or socio-demographic features associated with the individual, determining a metric based on the measured physiological or behavioral data, and determining the score by comparing the metric against a predicted value from a prediction model trained with the contextual data.

Example 2 relates to the method of Example 1, wherein measuring the at least one physiological or behavioral parameter comprises measuring the parameter with one or more sensors of an technical device associated with the individual.

Example 3 relates to the method of Example 2, wherein the technical device comprises at least one of a smart-phone, a camera, a microphone, a wearable device configured to detect body signals of the individual, an technical device implanted in the body of the individual, such as RFID devices, for example.

Example 4 relates to the method of any one of Examples 1 to 3, wherein measuring the at least one physiological or behavioral parameter comprises measuring the parameter in a hospital, at home, at a workplace, or during commuting of the individual. In general, the at least one physiological or behavioral parameter may be measured at any place where the individual is resting. Thus, the at least one physiological or behavioral parameter may be measured during a resting phase of the individual.

Example 5 relates to the method of any one of Examples 1 to 4, wherein measuring the at least one physiological or behavioral parameter comprises measuring the parameter during working hours and/or during resting hours of the individual.

Example 6 relates to the method of any one of Examples 1 to 5, wherein measuring the at least one physiological or behavioral parameter comprises measuring at least one of a heart rate, heart rate variability, sleep apnea events, time to fall asleep, blood pressure, body temperature, movement pattern, speech, respiration rate, social contacts.

Example 7 relates to the method of any one of Examples 1 to 6, wherein determining contextual data comprises associating a personal identifier of the individual with the individual dataset.

Example 8 relates to the method of Example 7, wherein determining contextual data comprises adding, based on the personal identifier, socio-demographic features of the individual to an individual dataset.

Example 9 relates to the method of Example 8, wherein the socio-demographic features of the individual are extracted from at least one of a human resources database or a doctor.

Example 10 relates to the method of any one of Examples 1 to 9, wherein the socio-demographic features comprise at least one of an age, gender, number of children, job position, salary of the individual, a body mass index, current medication, anamnesis, size of country, size of city, income, education level.

Example 11 relates to the method of any one of Examples 1 to 10, further comprising applying one or more privacy preservation algorithms to the contextual data.

Example 12 relates to the method of Example 11, wherein the privacy preservation algorithms comprise at least one of a blockchain algorithm, a local differential privacy algorithm or a multi-party computation algorithm.

Example 13 relates to the method of any one of Examples 1 to 12, further comprising training model parameters of the prediction model based on contextual data of a plurality of individuals.

Example 14 relates to the method of Example 13, wherein training the model parameters is performed at a central entity and wherein, after training, the trained model parameters and/or a predicted physiological or behavioral parameter are provided from the central entity to a personal device of the individual for comparing the metric against the predicted value.

Example 15 relates to the method of any one of Examples 1 to 14, wherein determining the score comprises feeding the contextual data in a trained prediction model to generate the predicted value (predicted metric) based on the contextual data.

Example 16 relates to the method of Example 15, wherein determining the score comprises computing a difference or ratio between the metric and the predicted value (predicted metric).

Example 17 relates to the method of any one of Examples 1 to 16, further comprising aggregating scores of different associated individuals to a group score.

Example 18 relates to the method of Example 17, wherein aggregating the individual scores comprises applying one or more privacy preservation algorithms to the individual scores.

Example 18 relates to the method of Example 17 or 18, further comprising certifying a group of associated individuals if its associated group score meets a predefined target.

Example 20 relates to a system for providing a score indicative of a physiological condition of at least one individual, wherein the system is configured to measure physiological or behavioral data of the individual, determine contextual data comprising a measurement context and/or socio-demographic features associated with the individual, determine a metric based on the measured physiological or behavioral data, and determine the score by comparing the metric against a predicted value from a prediction model trained with the contextual data.

The aspects and features described in relation to a particular one of the previous examples may also be combined with one or more of the further examples to replace an identical or similar feature of that further example or to additionally introduce the features into the further example.

Examples may further be or relate to a (computer) program including a program code to execute one or more of the above methods when the program is executed on a computer, processor or other programmable hardware component. Thus, steps, operations or processes of different ones of the methods described above may also be executed by programmed computers, processors or other programmable hardware components. Examples may also cover program storage devices, such as digital data storage media, which are machine-, processor- or computer-readable and encode and/or contain machine-executable, processor-executable or computer-executable programs and instructions. Program storage devices may include or be digital storage devices, magnetic storage media such as magnetic disks and magnetic tapes, hard disk drives, or optically readable digital data storage media, for example. Other examples may also include local computer devices (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system may comprise any circuit or combination of circuits. In one embodiment, the computer system may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system may also include a display device, one or more speakers, and a keyboard and/or controller, which can include a mouse, trackball, touch screen, voice-recognition device, or any other device that permits a system user to input information into and receive information from the computer system.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a nontransitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

It is further understood that the disclosure of several steps, processes, operations or functions disclosed in the description or claims shall not be construed to imply that these operations are necessarily dependent on the order described, unless explicitly stated in the individual case or necessary for technical reasons. Therefore, the previous description does not limit the execution of several steps or functions to a certain order. Furthermore, in further examples, a single step, function, process or operation may include and/or be broken up into several sub-steps, -functions, -processes or -operations.

If some aspects have been described in relation to a device or system, these aspects should also be understood as a description of the corresponding method. For example, a block, device or functional aspect of the device or system may correspond to a feature, such as a method step, of the corresponding method. Accordingly, aspects described in relation to a method shall also be understood as a description of a corresponding block, a corresponding element, a property or a functional feature of a corresponding device or a corresponding system.

The following claims are hereby incorporated in the detailed description, wherein each claim may stand on its own as a separate example. It should also be noted that although in the claims a dependent claim refers to a particular combination with one or more other claims, other examples may also include a combination of the dependent claim with the subject matter of any other dependent or independent claim. Such combinations are hereby explicitly proposed, unless it is stated in the individual case that a particular combination is not intended. Furthermore, features of a claim should also be included for any other independent claim, even if that claim is not directly defined as dependent on that other independent claim.

The invention claimed is:

1. A method for providing a score indicative of a physiological condition of at least one individual, the method comprising:

measuring, using one or more sensors of an electronic device associated with the individual, physiological or behavioral data of the individual;

determining contextual data comprising a measurement context and/or socio-demographic features associated with the individual;

adding controlled noise to the physiological or behavioral data of the individual and the contextual data;

removing a personal identifier from the physiological or behavioral data of the individual and the contextual data;

determining a metric based on the measured physiological or behavioral data;

training model parameters of a prediction model at a central entity using contextual data from a plurality of individuals;

providing the trained model parameters from the central entity to the electronic device of the individual;

determining the score by locally executing the prediction model on the electronic device to generate a predicted value based on the contextual data, and computing a difference between the metric and the predicted value;

aggregating scores of different associated individuals to a group score;

certifying a group of associated individuals if its associated group score meets a predefined target, the predefined target for certification being a quality of a working environment at a company for different scenarios; and providing the certified group score to the group of associated individuals while maintaining individual privacy by performing the score comparison locally on each individual's electronic device without transmitting raw physiological data to external servers.

2. The method of claim 1, wherein the electronic device comprises at least one of a smart-phone, a camera, a microphone, a wearable device configured to detect body signals of the individual, an electronic device implanted in the body of the individual.

3. The method of claim 1, wherein measuring the physiological or behavioral data comprises measuring the data in a hospital, at home, at a workplace, or during commuting of the individual.

4. The method of claim 1, wherein measuring the physiological or behavioral data comprises measuring the data during working hours and/or during resting hours of the individual.

5. The method of claim 1, wherein measuring the physiological or behavioral data comprises measuring at least one of a heart rate, heart rate variability, sleep apnea events, time to fall asleep, blood pressure, body temperature, movement pattern, speech, respiration rate, social contacts.

6. The method of claim 1, wherein determining the contextual data comprises associating a personal identifier of the individual with an individual dataset.

7. The method of claim 6, wherein determining the contextual data comprises adding, based on the personal identifier, socio-demographic features of the individual to the individual dataset.

8. The method of claim 7, wherein the socio-demographic features of the individual are extracted from at least one of a human resources database or acquired from a doctor.

9. The method of claim 1, wherein the socio-demographic features comprise at least one of an age, gender, number of children, job position, salary of the individual, a body mass index, current medication, anamnesis, size of country, size of city, income, education level.

10. The method of claim 1, further comprising applying one or more privacy preservation algorithms to the contextual data.

11. The method of claim 10, wherein the privacy preservation algorithms comprise at least one of a blockchain algorithm, a local differential privacy algorithm or a multi-party computation algorithm.

12. The method of claim 1, wherein comparing comprises feeding the contextual data in a trained prediction model to generate the predicted value based on the contextual data.

13. The method of claim 12, wherein comparing comprises computing a difference or ratio between the metric and the predicted value.

14. The method of claim 1, wherein aggregating the individual scores comprises applying one or more privacy preservation algorithms to the individual scores.

15. A system for providing a score indicative of a physiological condition of at least one individual, comprising:

one or more sensors of an electronic device associated with the individual; and processing circuitry configured to measure, using the one or more sensors, physiological or behavioral data of the individual, add controlled noise to the physiological or behavioral data of the individual and the contextual data, remove a personal identifier from the physiological or behavioral data of the individual and the contextual data, determine contextual data comprising a measurement context and/or socio-demographic features associated with the individual, determine a metric based on the measured physiological or behavioral data, train model parameters of a prediction model at a central entity using contextual data from a plurality of individuals, provide the trained model parameters from the central entity to the electronic device of the individual, determine the score by locally executing the prediction model on the electronic device to generate a predicted value based on the contextual data, and computing a difference between the metric and the predicted value, aggregate scores of different associated individuals to a group score; and certify a group of associated individuals if its associated group score meets a predefined target, the predefined target for certification being a quality of a working environment at a company for different scenarios, and provide the certified group score to the group of associated individuals while maintaining individual privacy by performing the score comparison locally on each individual's electronic device without transmitting raw physiological data to external servers.

\* \* \* \* \*